(12) United States Patent
Ogura (10) Patent No.: US 8,492,717 B2
(45) Date of Patent: Jul. 23, 2013

(54) PORTABLE RADIOGRAPHIC IMAGE CAPTURE DEVICE

(75) Inventor: Ryosuke Ogura, Tokyo (JP)

(73) Assignee: FUJIFILM Corporation, Toyko (JP)

( * ) Notice: Subject to any disclaimer, the term of this patent is extended or adjusted under 35 U.S.C. 154(b) by 164 days.

(21) Appl. No.: 13/082,667

(22) Filed: Apr. 8, 2011

(65) Prior Publication Data

US 2011/0248173 A1   Oct. 13, 2011

(30) Foreign Application Priority Data

Apr. 12, 2010   (JP) .................................. 2010-091803

(51) Int. Cl.
*G01J 1/00*   (2006.01)
(52) U.S. Cl.
USPC .......................... 250/336.1; 378/182; 378/189
(58) Field of Classification Search
USPC ........... 250/361, 336, 336.1, 361 R; 378/182, 378/189
See application file for complete search history.

(56) References Cited

U.S. PATENT DOCUMENTS

| | | | | |
|---|---|---|---|---|
| 4,457,010 A | * | 6/1984 | Jenkins et al. ................. | 378/167 |
| 5,912,944 A | * | 6/1999 | Budinski et al. .............. | 378/182 |
| 6,867,418 B2 | * | 3/2005 | Suzuki et al. ................. | 250/368 |
| 6,891,164 B2 | * | 5/2005 | Suzuki ..................... | 250/370.11 |
| 6,919,569 B2 | * | 7/2005 | Homme et al. .......... | 250/370.11 |
| 7,582,877 B2 | * | 9/2009 | Dobrusskin et al. ..... | 250/370.09 |
| 8,256,957 B1 | * | 9/2012 | Barnes et al. ................. | 378/189 |
| 2002/0181659 A1 | * | 12/2002 | Watanabe et al. ............. | 378/189 |
| 2007/0272873 A1 | * | 11/2007 | Jadrich et al. ............ | 250/370.11 |
| 2009/0190932 A1 | * | 7/2009 | Nishino et al. ................. | 398/140 |
| 2010/0038549 A1 | * | 2/2010 | Nishino et al. .......... | 250/370.09 |
| 2010/0054399 A1 | * | 3/2010 | Nishino et al. .................. | 378/28 |
| 2010/0207032 A1 | * | 8/2010 | Tsubota et al. .......... | 250/370.09 |

FOREIGN PATENT DOCUMENTS

JP        2006-242702 A       9/2006

* cited by examiner

*Primary Examiner* — David Porta
*Assistant Examiner* — Taeho Jo
(74) *Attorney, Agent, or Firm* — Sughrue Mion, PLLC (57) ABSTRACT

A portable radiographic image capture device including a radiation detector for capturing a radiographic image representing irradiated radiation and outputting an electrical signal representing the captured radiographic image; a control board that controls the image capture operation of the radiation detector; and a casing formed in a substantially rectangular flat plate shape, housing the radiation detector and the control board such that they are superimposed on each other. The casing has a flat image capture region for capturing a radiographic image with the radiation detector, is sloped such that the thickness at an end section at least one edge of the casing gradually decreases, and is capable of disposing at least a portion of at least one of the radiation detector and/or the control board inside the angled sloping region of the casing.

13 Claims, 10 Drawing Sheets

EXEMPLARY
EMBODIMENT

FIG.9B

SLOPE: ABRUPT GRADIENT
(STRAIGHT LINE TYPE)

FIG.9C

SLOPE: SMALL GRADIENT
(STRAIGHT LINE TYPE)

FIG.9D

SLOPE: FULL RADIUS
TYPE

FIG.9E

SLOPE: ABRUPT GRADIENT
(CURVED TYPE)

FIG.9F

SLOPE: SMALL GRADIENT
(CURVED TYPE)

FIG.10

PORTABLE RADIOGRAPHIC IMAGE CAPTURE DEVICE

CROSS-REFERENCE TO RELATED APPLICATION

This application is based on and claims priority under 35 USC 119 from Japanese Patent Application No. 2010-091803 filed on Apr. 12, 2010, which is incorporated by reference herein.

BACKGROUND

1. Technical Field

The present invention relates to a portable radiographic image capture device.

2. Related Art

Recently, radiation detectors are starting to be applied that employ a FPD (Flat Panel Detector) or the like, are capable of directly converting radiation into digital data, and have a radiation sensitive layer disposed on a Thin Film Transistor (TFT) active matrix board. Such radiation detectors have the advantage that, in comparison to previous imaging plates, images can be more immediately examined and video images can also be examined. As the radiation conversion method employed with such radiation detectors there is, for example an indirect conversion method in which radiation is first converted into light with a scintillator, then the converted light is converted into charge in a semiconductor layer such as a photodiode, and a direct conversion method in which radiation is converted directly into charge in a semiconductor layer, such as amorphous selenium. Various materials exist that can be employed for the semiconductor layers in each of the methods.

Portable radiographic image capture devices (also sometimes referred to below as electronic cassettes) are also being put into practice that are installed with a radiation detector and store radiographic image data output from the radiation detector.

Since such electronic cassettes are portable, a patient can remain on a stretcher or bed during image capture, and the image capture location can also be adjusted by changing the position of the electronic cassette. Accordingly, flexible in treatment can be attained for immobile patients.

However, since such electronic cassettes are carried around, consideration should be given to careless dropping and associated impacts. Japanese Patent Application Laid-Open (JP-A) No. 2006-242702 describes technology for protecting the configuration elements within a casing even when such an unanticipated event occurs. In this technology, a shock absorption member is provided to side faces of a flat plate rectangular shaped casing in which a radiation detector and a control board are housed. The thickness of this shock absorbing member decreases on progression away from the side faces of the electronic cassette. The result is an electronic cassette that is more difficult to tuck under a patient during image capture.

External sizes of cassettes are specified by Japanese Industrial Standard (JIS) Z4905, and imaging tables for housing cassettes are formed with housing sections that conform to this standard.

Accordingly, when cassettes are made so as to be capable of housing in housing sections complying to this standard, the cassettes cannot be made any larger than the respective specified size. Consequently, when an impact absorbing member is provided at the side faces of the cassette, the size of the space in the casing available for housing the radiation detector and the control board is decreased by the amount occupied by the impact absorbing member.

SUMMARY

In consideration of the above circumstances, the present invention provides a portable radiographic image capture device that can suppress any reduction in volume within a casing while also suppressing a reduction in handling characteristics.

A portable radiographic image capture device according to a first aspect of the present invention includes a radiation detector for capturing a radiographic image representing irradiated radiation and outputting an electrical signal representing the captured radiographic image; a control board that controls the image capture operation of the radiation detector; and a casing formed in a substantially rectangular flat plate shape, housing the radiation detector and the control board such that they are superimposed on each other. The casing has a flat image capture region for capturing a radiographic image with the radiation detector, is sloped such that the thickness at an end section at least one edge of the casing gradually decreases, and is capable of disposing at least a portion of at least one of the radiation detector and/or the control board inside the angled sloping region of the casing.

BRIEF DESCRIPTION OF THE DRAWINGS

Exemplary embodiments of the present invention will be described in detail based on the following figures, wherein.

DETAILED DESCRIPTION

Explanation follows regarding examples of a portable radiographic image capture device according to exemplary embodiments of the present invention, with reference to FIG. 1 to FIGS. 9A to 9F. The arrow UP in the drawings illustrates the vertical direction top.

Overall Configuration

Figure 1:
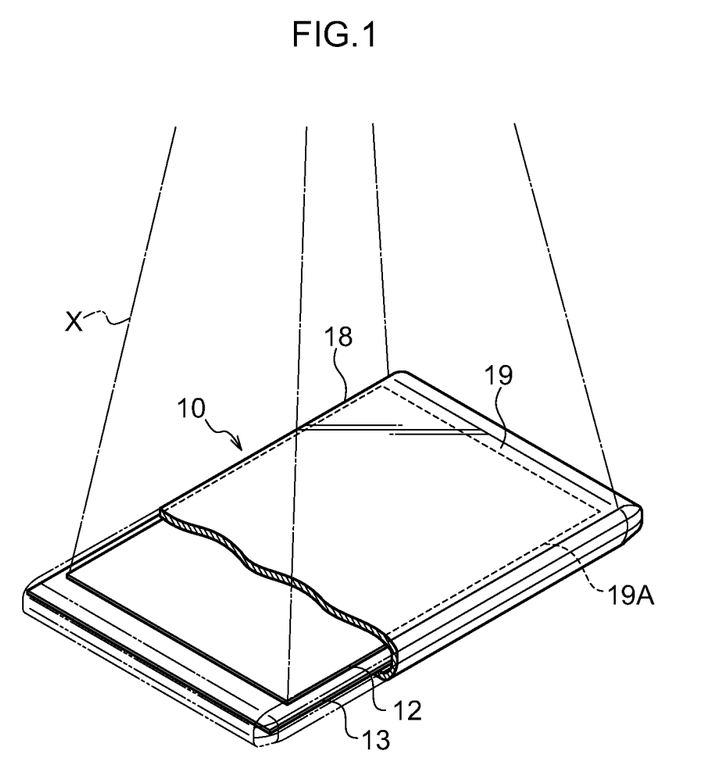
FIG. 1 is a cut-way perspective view showing an internal configuration of a portable radiographic image capture device according to an exemplary embodiment.

An internal configuration of a portable radiographic image capture device 10 (a so-called electronic cassette) according to the present exemplary embodiment is illustrated in FIG. 1.

The portable radiographic image capture device 10 according to the present exemplary embodiment is provided with a radiation detector 12 for detecting X-rays that have passed through a patient and a control board 13, described later, housed in sequence within a casing 18 from an irradiation face 19 of the casing 18 onto which X-rays are irradiated. The irradiation face 19 is configured with an imaging region 19A corresponding to the range where the radiation detector 12 is disposed, and configuring a region where a radiographic image is captured by the radiation detector 12.

Figure 2:
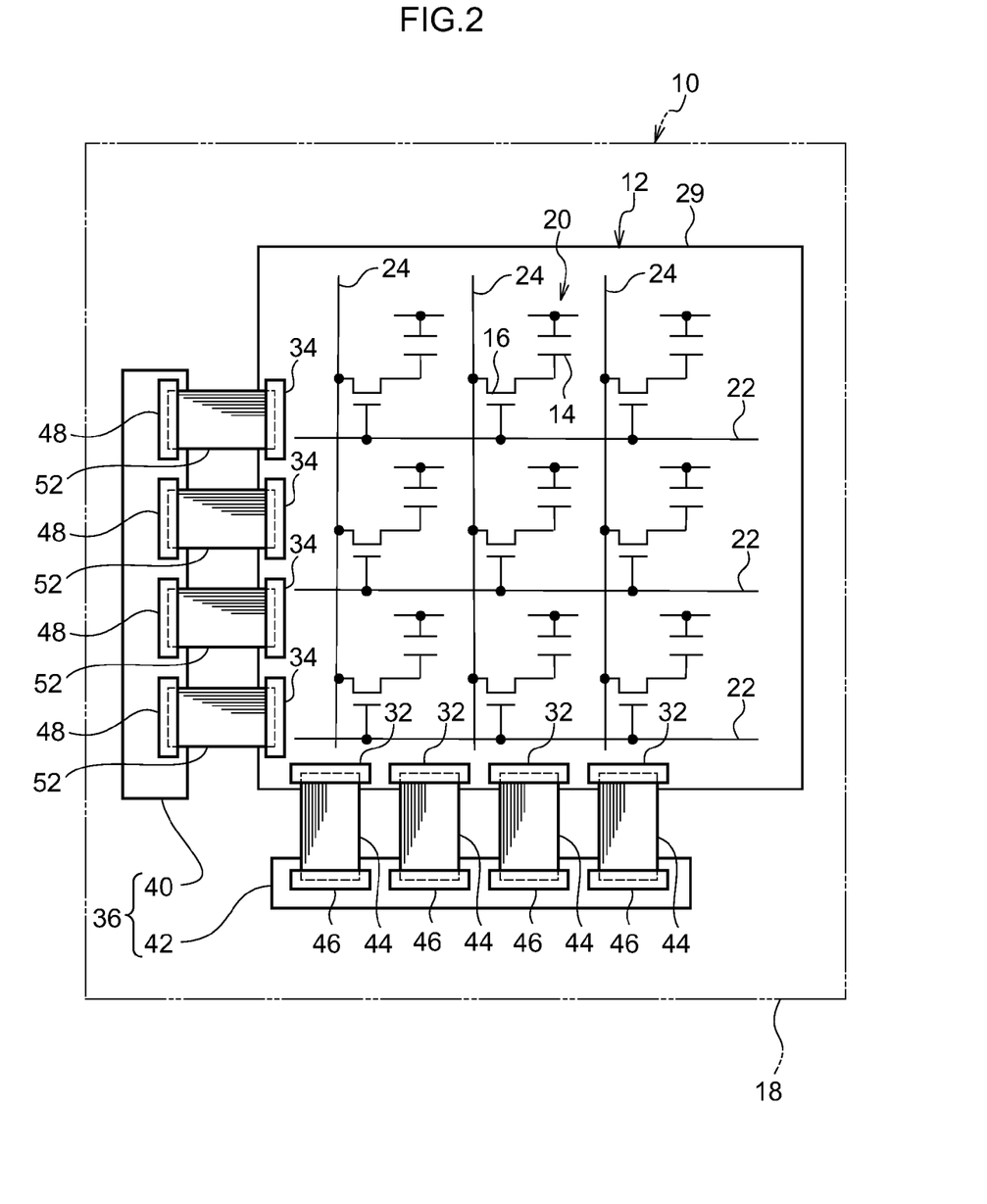
FIG. 2 is a circuit diagram illustrating a portable radiographic image capture device according to an exemplary embodiment.

The radiation detector 12 is, as shown in FIG. 2, provided with an Thin Film Transistor (TFT) active matrix board 29 (referred to below as a TFT board) having plural pixels 20 disposed in a two dimensional array. Each of the pixels 20 is configured with a sensor portion 14, which includes an upper electrode, a semiconductor layer and a lower electrode, and receives light and accumulates charge, and a TFT switch 16 for reading out the charge accumulated in the respective sensor portion 14.

The TFT board 29 is provided with plural scan lines 22 for switching the TFT switches 16 ON/OFF, and with plural signal lines 24 for reading out charge accumulated in the sensor portions 14. The scan lines 22 and the signal lines 24 are disposed so as to intersect with each other.

Figure 3:
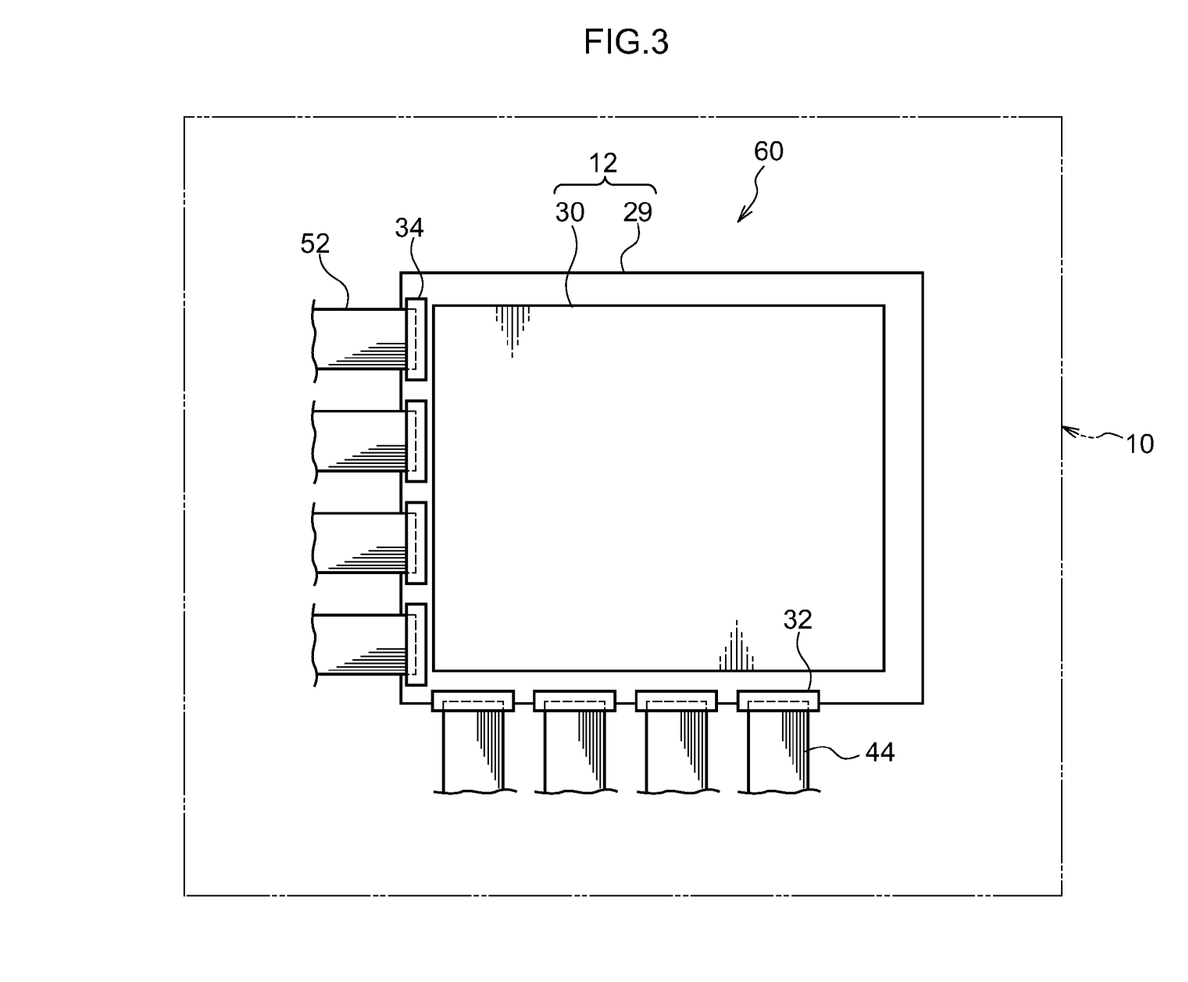
FIG. 3 is a plan view showing a portable radiographic image capture device according to an exemplary embodiment.
Figure 4:
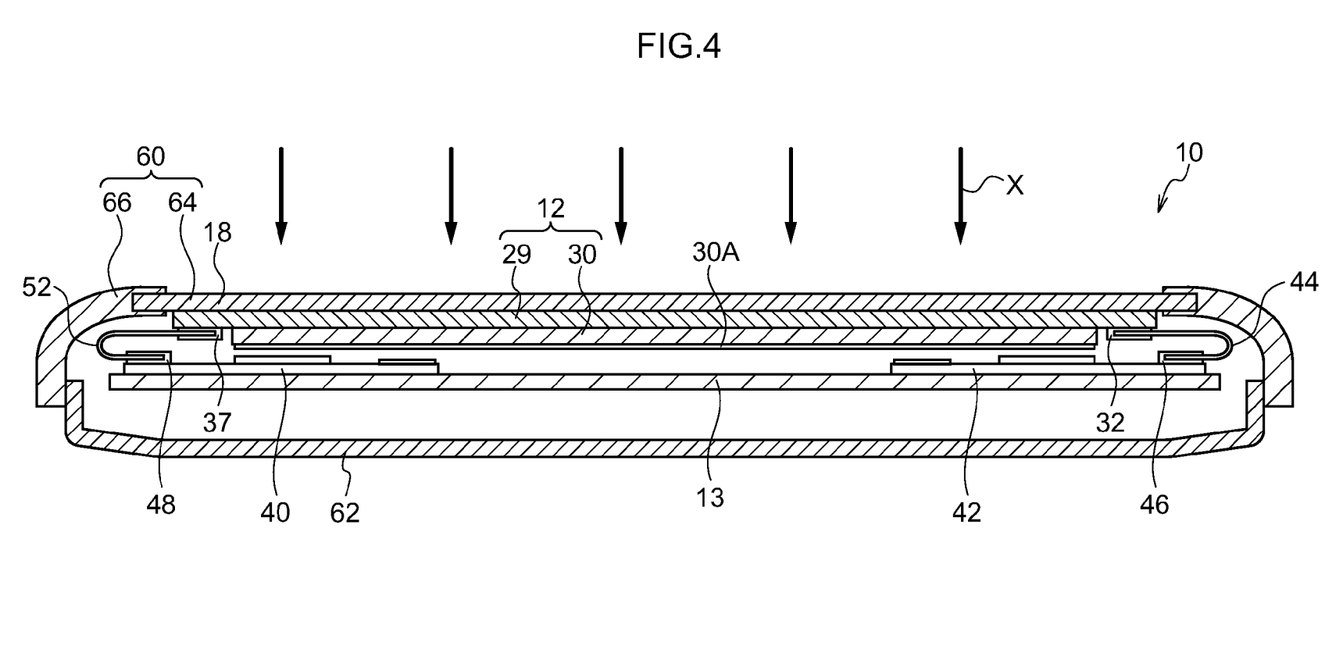
FIG. 4 is a cross-section illustrating a sectional configuration of a portable radiographic image capture device according to an exemplary embodiment.

The radiation detector 12 according to the present exemplary embodiment has a scintillator 30 attached to the surface of the TFT board 29 (see FIG. 3 and FIG. 4). The scintillator 30 is made from Gadolinium Oxy Sulfide (GOS), Cesium Iodide (CsI) or the like. The scintillator 30 has a light blocking body 30A (see FIG. 4) on the opposite face to the attached face of the radiation detector 12. The light blocking body 30A is for blocking generated light and stopping external leakage of generated light.

The radiation detector 12 converts irradiated radiation, such as X-rays, into light with the scintillator 30, and illuminates the light onto the sensor portions 14. The sensor portions 14 received the illuminated light from the scintillator 30 and accumulate charge.

Configuration is made such that by then switching ON the TFT switches 16, electrical signals (image signals) representing a radiographic image and corresponding to the charges that have been accumulated in the respective sensor portion 14 flow in each of the signal lines 24 for the signal lines 24 connected to the TFT switches 16 that have been switched ON.

Plural individual line connection connectors 32 are provided in a row at one signal line direction end of the radiation detector 12, and plural individual connectors 34 are provided in a row at one scan line direction end of the radiation detector 12. Each of the signal lines 24 is connected to one of the connectors 32 and each of the scan lines 22 is connected to one of the connectors 34.

The casing 18 is formed in a rectangular flat plate shape and, as shown in FIG. 4, internally houses the radiation detector 12 and the control board 13, for performing various types of control, such as of the image capture operation of the radiation detector 12 and of communication with an external device, superimposed on each other. Note that in the present exemplary embodiment, the radiation detector 12 is disposed such that the TFT board 29 makes contact with the inside face of the casing 18 on the irradiation face 19 side. Accordingly, radiation irradiated from the irradiation face 19 side passes through the TFT board 29 before being irradiated onto the scintillator 30.

In instances when the radiation detector 12 is irradiated with radiation from the face on the side to which the scintillator 30 is bonded (front face irradiation), there is more intense light generation at the top face side of the scintillator 30 (the opposite side to that of the TFT board 29). However, in instances when radiation is irradiated from the back side from the face not bonded to the scintillator 30 (back face irradiation), radiation that has passed through the TFT board 29 is irradiated onto the scintillator 30, and light generation is more intense at the TFT board 29 side of the scintillator 30. Charge is generated by the light generated in the scintillator 30 in each of the sensor portions 14. Accordingly, it is possible to design the radiation detector 12 with a higher sensitivity to radiation when radiation is irradiated from the front side than when radiation is irradiated from the back side, since radiation does not pass through the TFT board 29. However, the resolution of the radiographic images obtained by image capture is higher when radiation is irradiated from the back side compared to when radiation is irradiated from the front side, since the light generation position in the scintillator 30 is nearer with respect to each of the sensor portions 14. While the radiation detector 12 is disposed in the present exemplary embodiment for back face irradiation when radiation is irradiated from the irradiation face 19 side, the radiation detector 12 may be disposed for front face irradiation.

A control section 36 is provided to the control board 13 for controlling image capture operation with the radiation detector 12 and performing signal processing on the electrical signals flowing in each of the signal lines 24. The control section 36 includes a signal detection circuit 42 and a scan signal control circuit 40.

Plural individual connectors 46 are provided to the signal detection circuit 42 and one end of respective flexible cables 44 is electrically connected to the connectors 46. The other end of the flexible cables 44 is connected to the respective connectors 32. The signal detection circuit 42 is installed with an amplification circuit for each of the signal lines 24, for amplifying input electrical signals. Due to such a configuration, the signal detection circuit 42 detects the charge amounts accumulated in each of the sensor portions 14 as data for each of the pixels 20 configuring an image by detecting the electrical signals input by each of the signal lines 24 and amplified by the amplification circuits.

Connectors 48 are provided to the scan signal control circuit 40, and one end of respective flexible cables 52 is electrically connected to the connectors 48. The other end of the flexible cables 52 is connected to the respective connectors 34. Configuration is made such that the scan signal control circuit 40 outputs control signals to the scan lines 22 for switching the TFT switches 16 ON/OFF.

In order to capture a radiographic image, X-rays that have passed through a subject (patient) are irradiated onto the radiation detector 12.

The irradiated radiation, such as X-rays, are converted into light by the scintillator 30 and illuminated onto the sensor portions 14. The sensor portions 14 receive the light illuminated from the scintillator 30 and accumulate charge.

As shown in FIG. 2, during image readout, an ON signal (+10 to 20V) is applied from the scan signal control circuit 40 to the gate electrodes of the TFT switches 16 of the radiation detector 12, in sequence through the scan lines 22. By thus switching the TFT switches 16 of the radiation detector 12 ON in sequence, electrical signals according to the charge amount accumulated in the sensor portions 14 flow in the signal lines 24. The signal detection circuit 42 detects the charge amount accumulated in the sensor portions 14 as data for each of the pixels 20 configuring an image, based on the electrical signals flowing out through the signal lines 24 of the radiation detector 12. Image data is thereby obtained of an image representing the radiation irradiated onto the radiation detector 12.

In order to enhance handling characteristics, the portable radiographic image capture device 10 according to the present exemplary embodiment has a casing 18 formed with bevels at end sections of each of the four side faces of the casing 18, such that the thickness at the end sections is thinner than the thickness at the central portion of the casing 18.

Figure 5:
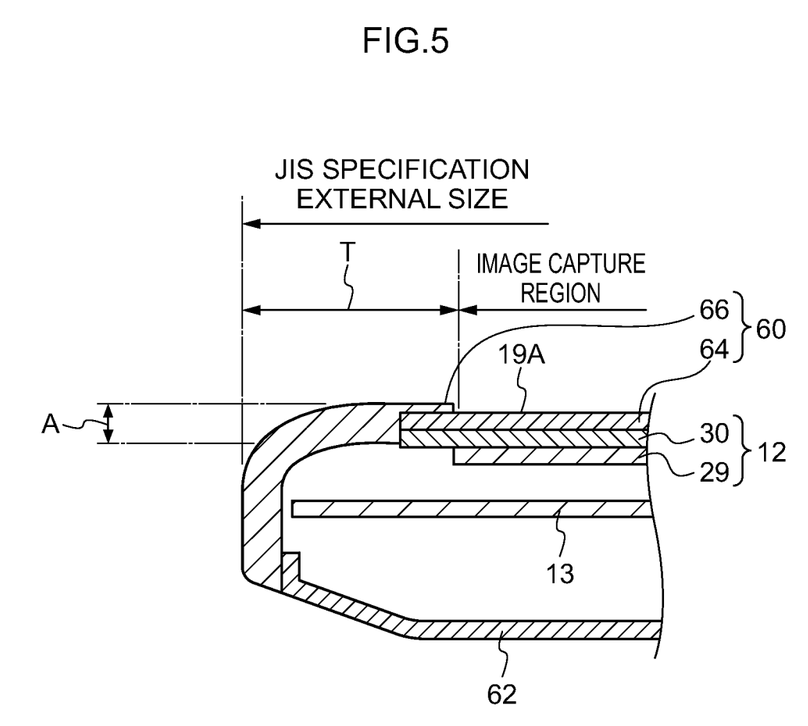
FIG. 5 is an enlarged cross-section showing an enlarged portion of an end section of a portable radiographic image capture device according to an exemplary embodiment.

An outline cross-section configuration of an end section of the portable radiographic image capture device 10 according to the present exemplary embodiment is illustrated in FIG. 5.

The casing 18 is provided with a front panel 60 on the subject side, and a back panel 62 on the opposite side to that of the subject, with the front panel 60 and the back panel 62 facing each other. The front panel 60 is configured by a top plate 64 and a support portion 66 that supports the top plate 64. The radiation detector 12 is provided on the face of the top plate 64 that is on the back panel 62 side.

The top plate 64 is made from a carbon composite in the present exemplary embodiment. Strength thereby secured while suppressing radiation absorption. The support portion 66 and the back panel 62 are made from an ABS resin.

The top plate 64 configures the imaging region 19A, this being the region of image capture where a radiographic image is captured by the radiation detector 12.

The support portion 66 is sloped such that the thickness of the casing 18 gradually gets thinner in a range T from the edge of the imaging region 19A up to the end of the casing 18. By sloping portions of the end sections of the casing 18 thus, the strength of the angled sloped regions is made higher than the strength of the image capture region. In the present exemplary embodiment, sloping is made so as to be gentle in the vicinity of the edge of the imaging region 19A and decrease steeply in the vicinity of the ends of the casing 18, with sloping made such that the thickness gradually decreases over the range T by thickness A, this being the thickness of the top plate 64 together with the TFT board 29. For example, for cases in which the respective thicknesses of the top plate 64 and the TFT board 29 are respectively 0.8 mm, sloping from the periphery of the imaging region 19A to the end section of the casing 18 is set at 1.6 mm thickness. Accordingly, even though the thickness of the casing 18 gradually decreases at the top plate 64 side by thickness A over the range T, the control board 13 can be disposed right up to the end section on the top plate 64 side. In the present exemplary embodiment, a portion of the TFT board 29 and the control board 13 is disposed inside the sloping region where the casing 18 is sloped.

The control board 13 here is a larger size than if a circuit was to be disposed in a planar configuration with the TFT board 29 in order try and achieve a thinner form.

The portable radiographic image capture device 10 can be made to the external sizes stipulated in JIS Z4905 by varying the size of the radiation detector 12. However, making a common control board 13 irrespective of the size of the radiation detector 12 is preferable from the manufacturing perspective, and for smaller sizes of the portable radiographic image capture device 10 this sometimes results in the control board 13 being larger than the radiation detector 12.

Consequently, achieving commonality of the control board 13 is facilitated by being able to dispose the control board 13 such that it can extend inside the casing 18 right across to the end section.

In the present exemplary embodiment, the back panel 62 is also sloped such that the thickness at the end sections of the portable radiographic image capture device 10 is reduced to 10 mm or less. For example, when the portable radiographic image capture device 10 is sized according to specification of type JC 35×43 under JIS Z4905, the thickness of the portable radiographic image capture device 10 is made at 14 mm, however the end sections of the back panel are sloped at such that the thickness of the portable radiographic image capture device 10 becomes only 10 mm at the end sections.

Note that configuration may be made with the support portion 66 not sloped and sloping only formed to the back panel 62. For the larger sizes of portable radiographic image capture device 10 out of the external sizes specified according to JIS Z4905, since there are cases when the control board 13 is smaller than the radiation detector 12, the range T from the edge of the imaging region 19A to the end of the portable radiographic image capture device 10 can be reduced to a minimum by not sloping the support portion 66. Namely, the imaging region 19A can be maximized, with good usability.

Explanation now follows regarding use of the portable radiographic image capture device 10 according to the present exemplary embodiment.

When an imaging technician is capturing a radiographic image, the portable radiographic image capture device 10 is disposed at the location for image capture on the patient, with the irradiation face 19 on the patient side.

Figure 6:
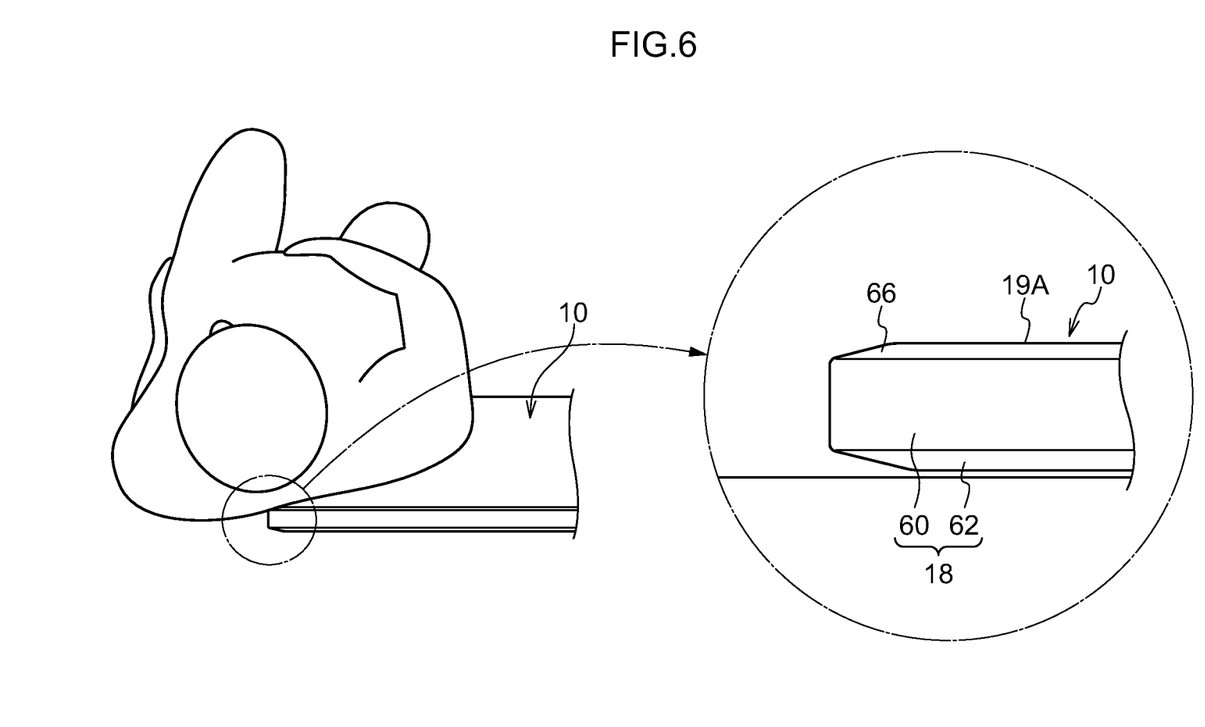
FIG. 6 is a diagram showing an example of a way in which a portable radiographic image capture device makes contact with a patient when tucked under the patient.

By disposing the portable radiographic image capture device 10 thus, as shown in FIG. 6, when the portable radiographic image capture device 10 is being tucked under the patient, the end section of the support portion 66 contacts the patient as the portable radiographic image capture device 10 is being tucked under, due to beveling the end section at the side face side of the casing 18 and sloping the support portion 66 of the front panel 60 as in the exemplary embodiment, thereby alleviating discomfort felt by the patient.

Figure 7:
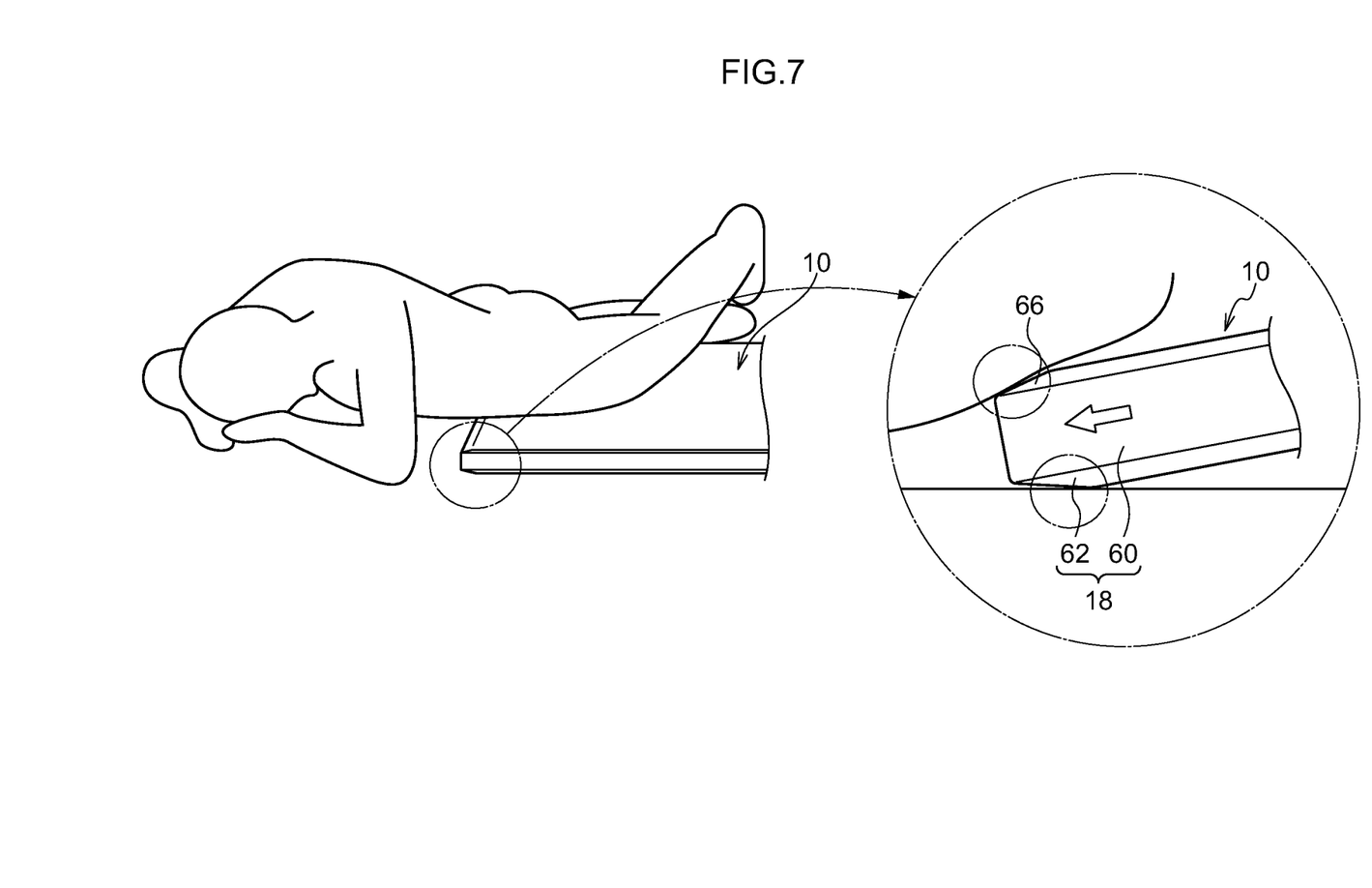
FIG. 7 is a diagram showing an example of a way in which a portable radiographic image capture device makes contact with a patient and with an underlying surface when tucked under the patient.

Sloping both the support portion 66 of the front panel 60 and the back panel 62 facilitates tucking under, as shown in FIG. 7.

Figure 8:
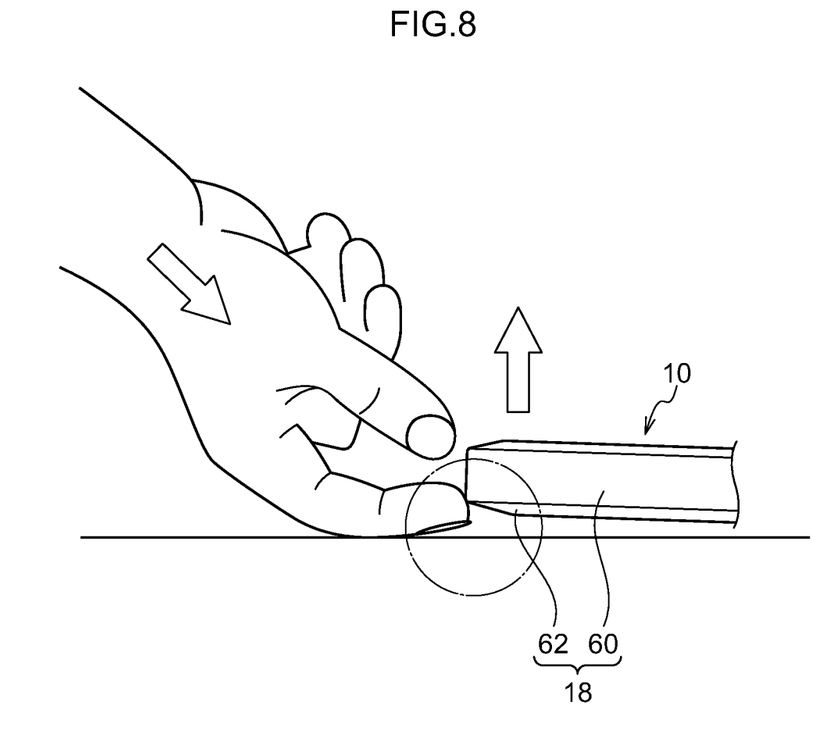
FIG. 8 is a diagram showing an example of a way in which a finger engages with a portable radiographic image capture device when picking up the device.

Moreover, sloping the back panel 62 also facilitates picking up since a finger can lift an end section when picking up the portable radiographic image capture device 10, as shown in FIG. 8.

According to the present exemplary embodiment, by sloping the end section of the four edges of the casing 18 as described above such that the thickness gradually decreases, since this enables a portion of at least one of the radiation detector 12 and/or the control board 13 to be disposed inside the angled sloping region, reduction in capacity inside the casing can be suppressed while also suppressing reduction in handling characteristics.

In the present exemplary embodiment, by also sloping the back panel 62 the thickness of the portable radiographic image capture device 10 at the end sections is reduced so as to be 10 mm or less. By thus making the thickness of the end sections for tucking under the patient during image capture 10 mm, any discomfort felt by the patient can be reduced. Note that configuration may be made such that the thickness of the end sections is thinner than 10 mm.

Note that in cases where the support portion 66 is not sloped and only the back panel 62 is sloped, since the portable radiographic image capture device 10 can be inclined when being tucked under a patient, any discomfort felt by a patient can be alleviated by flattening the angle with which the end section of the support portion 66 contacts the patient.

Note that while detailed explanation has been given regarding particular exemplary embodiments of the present invention, the present invention is not limited to these exemplary embodiments. It is clear to one skilled in the art that various other exemplary embodiments are possible within the scope of the present invention.

Figure 9A:
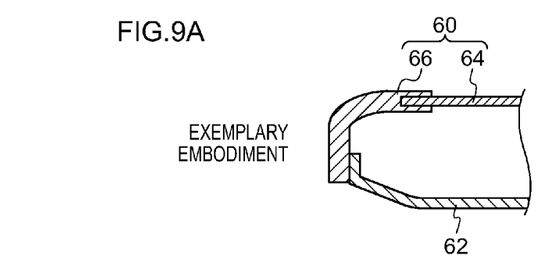
FIG. 9A to 9F illustrate cross-sections of portable radiographic image capture devices according to exemplary embodiments.
Figure 9B:
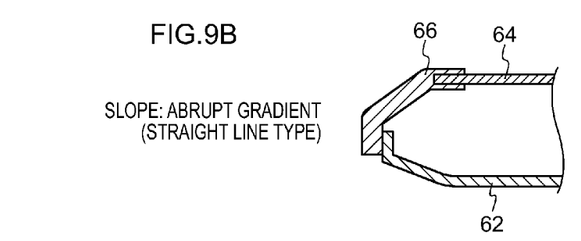
Figure 9C:
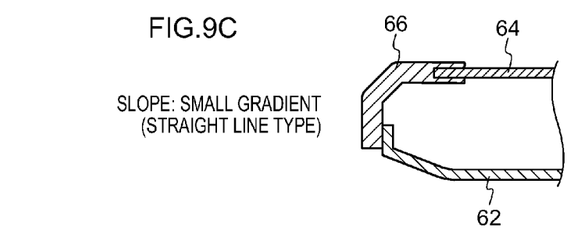
Figure 9D:
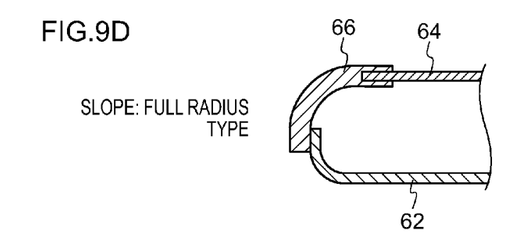
Figure 9E:
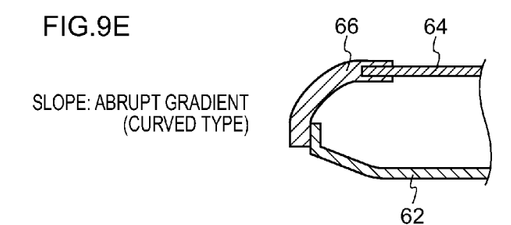
Figure 9F:
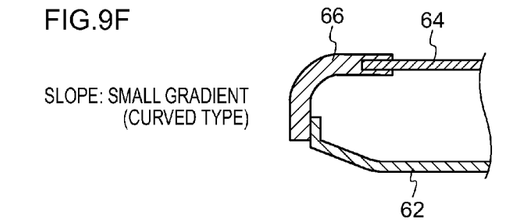

In the above exemplary embodiments, as shown in FIG. 9A, explanation has been given of a case in which the support portion 66 is sloped such there is gentle sloping in the vicinity of the edge within the range T from the edge of the imaging region 19A to the end of the support portion 66 and a rapid decrease at the vicinity of the end of the support portion 66, however the present invention is not limited to such an exemplary embodiment. For example, as shown in FIG. 9B, the support portion 66 may be sloped to give a straight-line profile between the edge of the imaging region 19A and the end of the support portion 66, with the angle of the support portion 66 changing at the edge of the imaging region 19A and at the end section of the support portion 66. Furthermore, as shown in FIG. 9C, the support portion 66 may be sloped with a short straight-line profile between the edge of the imaging region 19A and the end of the support portion 66. Or, as shown in FIG. 9D, the support portion 66 may be shaped with a radial profile overall between the edge of the imaging region 19A and the end of the support portion 66. Or, as shown in FIG. 9E, the support portion 66 may be sloped such that the thickness of the casing 18 gradually decreases between the edge of the imaging region 19A and the end of the support portion 66. Or, as shown in FIG. 9F, the support portion 66 may have a sudden change of angle at a portion between the edge of the imaging region 19A and the end of the support portion 66.

Figure 10:
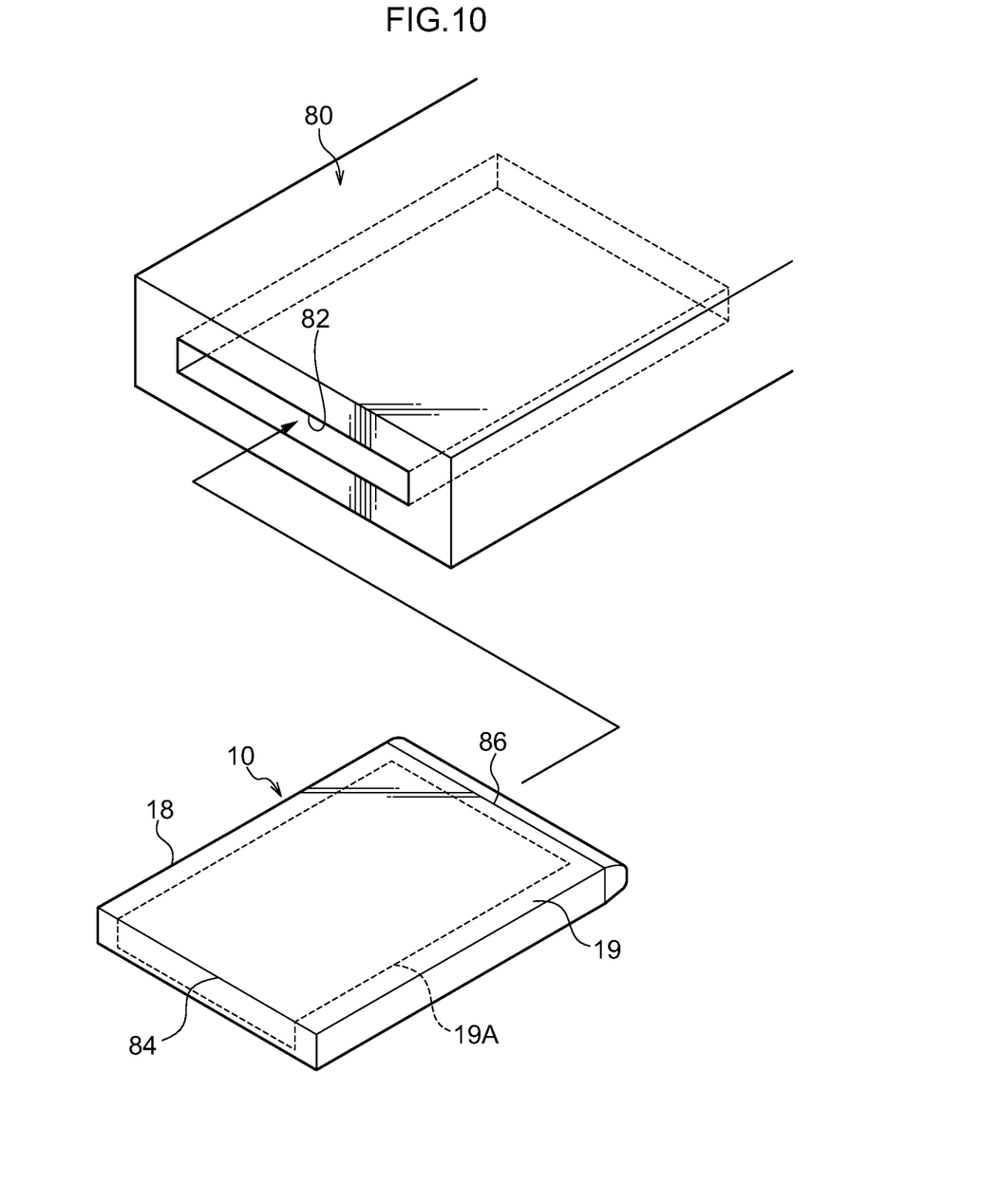
FIG. 10 is a perspective view illustrating an example of a mammography imaging table and a portable radiographic image capture device employed in mammography.

Explanation in the above exemplary embodiment is of a case in which beveling of end sections is performed at all four side face sides of the casing 18, however the present invention is not limited to this exemplary embodiment. As long as beveling is performed to the end section of at least one edge, handling characteristics can be enhanced at the beveled end section(s). Namely, for example configuration may be made with beveling at the end section at only one edge. For example, as shown in FIG. 10, consider a case in which the portable radiographic image capture device 10 is employed in mammography, a housing section 82 is provided to the side of an image capture table 80 at the front face where the patient is positioned during image capture, and the portable radiographic image capture device 10 is used by setting it in the housing section 82 from the front face side. In such a case, in order to set the portable radiographic image capture device 10 with the imaging region 19A close to the chest wall, preferably the side of an edge 84 on the patient side when the portable radiographic image capture device 10 is set in the image capture table 80 is not sloped, but the side of an edge 86, at the leading end when facing the edge 84 and setting in the image capture table 80, is sloped. Setting of the portable radiographic image capture device 10 in the image capture table 80 is facilitated in this manner. Or, for example, configuration may be made such that end sections at two adjacent edges are beveled. The handling characteristics can be accordingly enhanced when the portable radiographic image capture device 10 is being tucked under a patient, by tucking in from a beveled end section extending along either a length direction or width direction.

Furthermore, while explanation has been given in the above exemplary embodiment of a case configured with a single control board 13, the present invention is not limited to such an exemplary embodiment and the control board 13 may be divided into plural boards according to function.

According to the present invention, the casing is sloped such that the thickness at an end section at least one edge of the casing gradually decreases, and is capable of disposing at least a portion of at least one of the radiation detector and/or the control board inside the angled sloping region of the casing. Consequently, any reduction in volume within the casing can be suppressed while a reduction in handling characteristics is also suppressed.

In another aspect of the present invention, configuration may be made such that the end section at the at least one side of the casing is sloped from the edge of the image capture region.

In another aspect of the present invention, configuration may be made such that an end section of at least one further side is sloped on at least the front face and/or the back face of the casing formed in the substantially rectangular flat plate shape.

In another aspect of the present invention, configuration may be made such that the radiation detector includes, stacked on each other, a conversion layer that converts irradiated radiation into light and a detection board that detects the converted light, and the radiation detector is disposed such that the detection board makes contact with either the front face or the back face forming the substantially rectangular flat plate shape; and at the side of the casing where the detection board is disposed in contact the casing is sloped by substantially the combined thickness of the panel configuring the casing and the detection board.

In another aspect of the present invention, configuration may be made such that the sloping is made at the end sections of the casing on two adjacent sides.

In another aspect of the present invention, configuration may be made such that the sloping is made such that the thickness of the end section on at least one side reduces to 10 mm or less.

In another aspect of the present invention, configuration may be made such that the sloped end section of the casing is formed from a different member to that of the image capture region so as to cover the side face of the image capture region and give a higher strength than that of the image capture region.

According to the present invention, a reduction in volume within a casing can be suppressed while also suppressing a reduction in handling characteristics.

What is claimed is:

1. A portable radiographic image capture device comprising:
a radiation detector for capturing a radiographic image representing irradiated radiation and outputting an electrical signal representing the captured radiographic image;
a control board that controls the image capture operation of the radiation detector; and
a casing formed in a substantially rectangular flat plate shape, housing the radiation detector and the control board such that they are superimposed on each other, the casing having a flat image capture region for capturing a radiographic image with the radiation detector, the casing being sloped such that the thickness at an end section at least one edge of the casing gradually decreases forming a case sloping portion, and the casing configured to dispose at least a portion of at least one of: the radiation detector and the control board in the case sloping portion such that portion of the at least one of: the radiation detector and the control board overlaps the angled sloping region of the casing when viewed orthogonally with respect to the flat image capture region.

2. The portable radiographic image capture device of claim 1, wherein the end section at the at least one side of the casing is sloped from the edge of the image capture region.

3. The portable radiographic image capture device of claim 2, further wherein an end section of the back face, which is the side of the casing opposite from the image capture region, is sloped.

4. The portable radiographic image capture device of claim 3, wherein:
   the radiation detector comprises, stacked on each other, a conversion layer that converts irradiated radiation into light and a detection board that detects the converted light, and the radiation detector is disposed such that the detection board makes contact with either the front face or the back face forming the substantially rectangular flat plate shape; and
   at the side of the casing where the detection board is disposed in contact the casing is sloped by substantially the combined thickness of the panel configuring the casing and the detection board.

5. The portable radiographic image capture device of claim 4, wherein the sloping is made at the end sections of the casing on two adjacent sides.

6. The portable radiographic image capture device of claim 5, wherein the sloping is made such that the thickness of the end section on at least one side reduces to 10 mm or less.

7. The portable radiographic image capture device of claim 6, wherein the sloped end section of the casing is formed from a different member to that of the image capture region so as to cover the side face of the image capture region and give a higher strength than that of the image capture region.

8. The portable radiographic image capture device of claim 1, wherein an end section of the back face, which is the side of the casing opposite from the image capture region, is sloped.

9. The portable radiographic image capture device of claim 1, wherein:
   the radiation detector comprises, stacked on each other, a conversion layer that converts irradiated radiation into light and a detection board that detects the converted light, and the radiation detector is disposed such that the detection board makes contact with either the front face or the back face forming the substantially rectangular flat plate shape; and
   at the side of the casing where the detection board is disposed in contact the casing is sloped by substantially the combined thickness of the panel configuring the casing and the detection board.

10. The portable radiographic image capture device of claim 1, wherein the sloping is made at the end sections of the casing on two adjacent sides.

11. The device of claim 10, wherein a first adjacent side is disposed above the radiation detector and a second adjacent side is disposed below the radiation detector, the first and second adjacent sides sloping in a direction towards each other at a common end of the casing.

12. The portable radiographic image capture device of claim 1, wherein the sloping is made such that the thickness of the end section on at least one side reduces to 10 mm or less.

13. The portable radiographic image capture device of claim 1, wherein the sloped end section of the casing is formed from a different member to that of the image capture region so as to cover the side face of the image capture region and give a higher strength than that of the image capture region.

* * * * *